(12) United States Patent
Kim

(10) Patent No.: US 10,012,578 B2
(45) Date of Patent: Jul. 3, 2018

(54) PARTICULATE MATTER SENSOR

(71) Applicant: HYUNDAI MOTOR COMPANY, Seoul (KR)

(72) Inventor: Dong Gu Kim, Bucheon-si (KR)

(73) Assignee: Hyundai Motor Company, Seoul (KR)

( * ) Notice: Subject to any disclaimer, the term of this patent is extended or adjusted under 35 U.S.C. 154(b) by 414 days.

(21) Appl. No.: 14/853,942

(22) Filed: Sep. 14, 2015

(65) Prior Publication Data

US 2016/0153885 A1   Jun. 2, 2016

(30) Foreign Application Priority Data

Dec. 2, 2014   (KR) .......................... 10-2014-0170353

(51) Int. Cl.
*G01N 15/06* (2006.01)
*G01M 15/10* (2006.01)
*G01N 15/00* (2006.01)

(52) U.S. Cl.
CPC ...... *G01N 15/0656* (2013.01); *G01M 15/102* (2013.01); *G01N 15/0606* (2013.01); *G01N 2015/0046* (2013.01)

(58) Field of Classification Search
CPC ............ G01M 15/102; G01N 15/0656; G01N 15/0606; G01N 2015/0046
USPC ....................... 73/23.33, 28.01, 31.01, 31.02
See application file for complete search history.

(56) References Cited

U.S. PATENT DOCUMENTS

| | | | |
|---|---|---|---|
| 2011/0203348 A1* | 8/2011 | Hedayat | G01N 15/0656 73/23.33 |
| 2015/0000376 A1* | 1/2015 | Fix | H01L 21/3043 73/31.06 |

FOREIGN PATENT DOCUMENTS

| | | |
|---|---|---|
| JP | 2010-275977 A | 12/2010 |
| JP | 2013-068197 A | 4/2013 |
| JP | 2013-521469 A | 6/2013 |
| JP | 2014-084862 A | 5/2014 |
| KR | 2013-0065409 A | 6/2013 |

* cited by examiner

*Primary Examiner* — Daniel S Larkin
(74) *Attorney, Agent, or Firm* — McDermott Will & Emery LLP

(57) ABSTRACT

A particulate matter sensor includes a cartridge having an opening, and a substrate disposed inside the cartridge. A conductor is in contact with one surface of the substrate, has a plurality of penetration holes through a flow direction of the exhaust gas, and includes a plurality of cells formed therein with an electrode layer. The particulate matter sensor detects a particulate matter included in the exhaust gas based on a variation of resistance or capacitance.

13 Claims, 3 Drawing Sheets

PARTICULATE MATTER SENSOR

CROSS-REFERENCE TO RELATED APPLICATION

This application claims the benefit priority to of Korean Patent Application No. 10-2014-0170353 filed in the Korean Intellectual Property Office on Dec. 2, 2014, the entire content of which is incorporated herein by reference.

TECHNICAL FIELD

The present disclosure relates to a particulate matter sensor. More particularly, the present disclosure relates to a particulate matter sensor for an exhaust system of a vehicle which detects a particulate matter in order to detect an error of the diesel particulate.

BACKGROUND

As limitations in exhaust gas of a vehicle are reinforced, a post-processing device for cleaning exhaust gas has been developed.

Exhaust gas exhausted from a gasoline vehicle or a diesel vehicle using gasoline or diesel as a fuel includes carbon monoxide, hydrocarbons, nitrogen oxides, sulfur oxides, and particulate matter.

Particularly, a particulate matter (PM) in the diesel vehicle accelerates generation of a floating dust as a main cause of air pollution. Accordingly, limitation of the PM is very strict.

In order to reduce the PM in the diesel vehicle, a diesel particulate filter (DPF) is part of an exhaust system, and a particulate matter sensor is used to detect an amount of soot captured in the DPF.

The particulate matter sensor detects variation in resistance or capacitance generated when a particulate material included in exhaust gas is accumulated in the sensor, and is installed at a rear end of the DPF.

The particulate material sensor may be classified into an accumulation sensor and a real time sensor.

The accumulation particulate matter sensor is used for the majority of vehicle components, and detects variation of a current flow when the particulate matter is accumulated at two digital electrodes to which a voltage is applied.

Since the accumulation particulate matter sensor has a simple sensor configuration, reliability is high and a manufacturing cost is low so that the accumulation particulate matter sensor is suitable for the vehicle.

The real time particulate matter sensor may monitor an amount of a particulate matter in real time by detecting an ionization reaction of the particulate matter.

However, the particulate matter sensor according to the related as described above requires an initial accumulation time until a current variation signal is generated, and requires a complicated sensor structure for determining breakage of the diesel particulate filter.

Further, accuracy of the particulate matter sensor decreases and a size of the particulate matter sensor increases so that it is difficult to miniaturize the particulate matter sensor.

The above information disclosed in this Background section is only for enhancement of understanding of the background of the invention, and therefore, it may contain information that does not form the prior art that is already known in this country to a person of ordinary skill in the art.

SUMMARY

The present disclosure has been made in an effort to provide a particulate matter sensor having advantages of reducing an initial accumulation time by rapidly accumulating a particulate matter included in exhaust gas by applying a bottleneck structure to the particulate matter sensor for detecting the particulate matter, and then by measuring a variation in capacitance or resistance caused by the accumulated particulate matter.

According to an exemplary embodiment of the present inventive concept, a particulate matter sensor for an exhaust system of a vehicle includes a cartridge having an opening and a substrate disposed inside the cartridge. A conductor is in contact with one surface of the substrate, has a plurality of penetration holes through a flow direction of the exhaust gas, and includes a plurality of cells having an electrode layer. The particulate matter sensor detects a particulate matter included in the exhaust gas based on a variation of resistance or capacitance Each of the cells may have at least one slanted surface which has a width that gradually decreases in the direction of a rear surface from a front surface thereof.

Each cell may be formed at a front surface of the conductor by a wet etching process.

The substrate may have a plurality of substrate holes connected to the plurality of penetration holes, respectively.

A front surface of the conductor may be located at the opening inside the cartridge.

The conductor has a hot wire that may be installed at a rear surface thereof.

The hot wire may include a first hot wire formed in a longitudinal direction of the conductor. A second hot wire is connected to the first hot wire in a meandering form.

The substrate is in contact with the conductor through an adhesive layer.

The substrate may be made of a ceramic material.

Each cell may have at least one slanted surface formed by the wet etching of the conductor. The at least one slanted surface may have a slanted angle formed in accordance with a crystalline direction.

The penetration hole and the substrate hole may have a diameter of 12 μm to 20 μm.

The conductor may have a thickness of 500 μm.

According to the exemplary embodiment of the present inventive concept, the particulate matter sensor may measure a variation in capacitance to reduce an initial accumulation time by rapidly accumulating a particulate matter included in exhaust gas through applying a bottleneck structure to a sensor for detecting the particulate matter.

Accordingly, an algorithm for determining breakage of the diesel particulate filter may be optimized.

Further, 90% or more of the particulate matter may be captured by applying a structure similar to a diesel particulate filter.

Various other effects may be directly or indirectly disclosed in the following description of the embodiment of the present inventive concept.

That is, various other effects may be disclosed in a detailed description to be described below according to an exemplary embodiment of the present inventive concept.

DETAILED DESCRIPTION OF THE EMBODIMENTS

Figure 1:
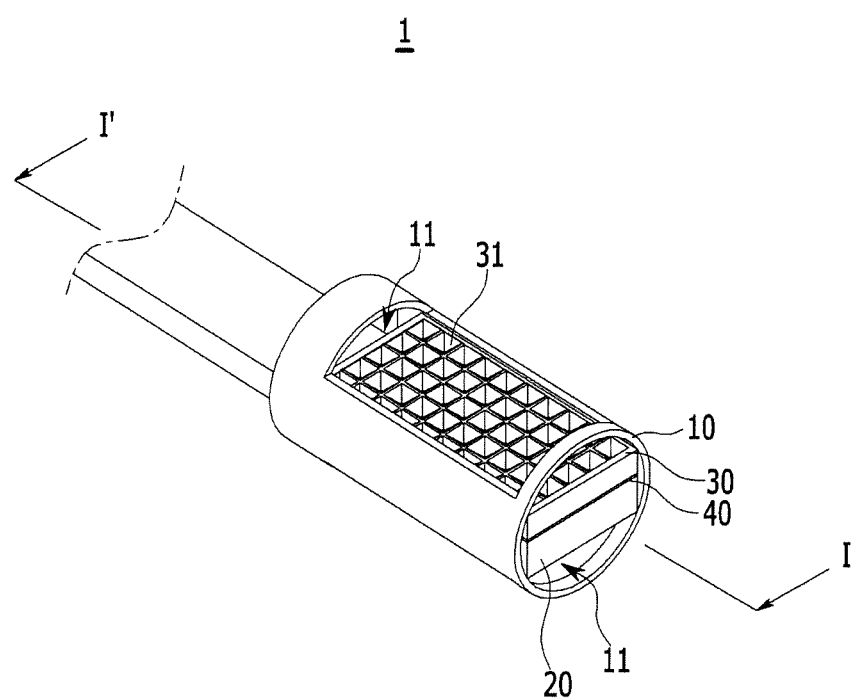
FIG. 1 is a perspective view illustrating a particulate matter sensor according to an exemplary embodiment of the present disclosure.

Hereinafter, an exemplary embodiment of the present inventive concept will be described with reference to the accompanying drawings.

Accordingly, the drawings and description are to be regarded as illustrative in nature and not restrictive. Like reference numerals designate like elements throughout the specification.

Figure 2:
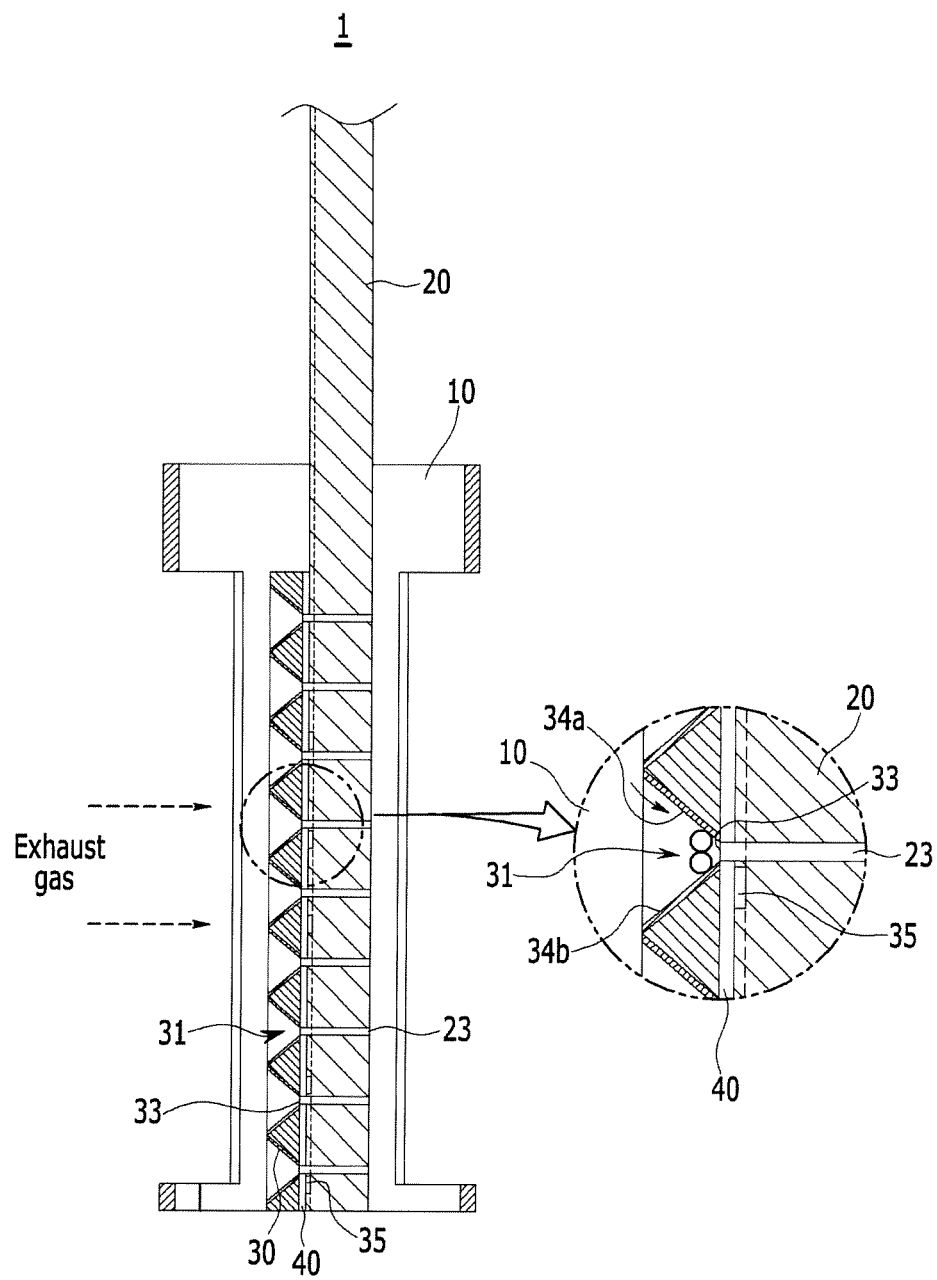
FIG. 2 is a cross-sectional view taken along the line I-I' of FIG. 1.

FIG. 1 is a perspective view illustrating a particulate matter sensor according to an exemplary embodiment of the present inventive concept, and FIG. 2 is a cross-sectional view taken along the line I-I' of FIG. 1.

Referring to FIGS. 1 and 2, a particulate matter sensor 1 according to an exemplary embodiment of the present inventive concept includes a cartridge 10, a substrate 20, and a conductor 30.

The cartridge 10 has a hollow cylindrical shape and has an opening 11 formed at both sides of the cartridge 10 corresponding to exterior circumferences, respectively.

Further, the substrate 20 is disposed inside the cartridge 10. The substrate 20 has a thin flat bar shape, and has a length longer than that of the cartridge 10. The substrate 20 may be made of a ceramic material. In addition, the substrate 20 has a substrate hole 23 having the same shape at a corresponding position of a penetration hole 33 to be described below.

The substrate hole 23 is formed corresponding to the number of penetration holes 33 which are formed at the conductor 30.

The conductor 30 is in contact with one surface of the substrate 20, and may have a thickness of 500 μm. However, the present disclosure is not limited thereto. That is, the thickness of the conductor 30 may be changed if necessary.

The conductor 30 makes contact with the substrate 20 so that a front surface of the conductor 30 is located at a corresponding part of the opening 11 of the cartridge 10.

An adhesive layer 40 is formed between the substrate 20 and the conductor 30 so that the substrate 20 makes contact with the conductor 30 by the adhesive layer 40.

The front surface of the conductor 30 is formed by a plurality of cells 31.

Each cell 31 is formed by slanted surfaces that have a width gradually decreasing in a direction toward a rear surface from a front surface.

The exhaust gas is introduced through the front surface of the cell 31 and exhausts through the rear surface of the cell 31.

That is, the slanted surfaces of the cell 31 are inclined in the direction in which the exhaust gas flows and has a shape gradually decreasing.

A center of the cell 31 has the penetration hole 33 through the conductor 30.

The cell 31 may be formed by wet etching the conductor 30, and the slanted surfaces may have an angle of, for example, 54.7°. However, the present disclosure is not limited thereto if necessary. That is, an angle of the slanted surfaces of the cell 31 may change if necessary. When a material is wet-etched, a slant slope may be dependent on a crystalline direction of the material. For example, when the conductor 30 is formed from a silicon wafer, the angle of 54.7° may be formed. A different angle may be formed by using a different material, and the angle of the slant surface may be formed in accordance with the crystalline structure of the conductor 30.

The conductor 30 is formed so that the plurality of cells 31 are closed in four directions to fill the entire surface, and penetration holes 33 corresponding to the number of the cells 31 are formed through the conductor 30.

When the exhaust gas flows, the penetration hole 33 introduces a bottleneck phenomenon to accumulate the particulate matter on the slanted surfaces, and the gas from which the particulate matter is separated exhausts through the penetration hole 33 and the substrate hole 23.

Further, although the above embodiment describes that the penetration hole 33 and the substrate hole 23 have a size (diameter) of 12 μm, the present disclosure is not limited thereto. That is, sizes of the penetration hole 33 and the substrate hole may be changed if necessary. More specifically, the size of the holes 33 and 23 may be decided considering easy collecting of the particulate matter and a smooth flow of the exhaust gas. The size of the holes 33 and 23 may be 12 μm to 20 μm. The exhaust gas may not smoothly flow through the holes 33 and 23 when the diameters of the holes 33 and 23 are excessively small, and the particulate matter may not be easily collected in the cell 31 when the diameters are excessively large.

The slanted surfaces are formed in a way opposing each other, electrode layers 34a and 34b are respectively formed at the opposing slanted surfaces. When the particulate matter does not pass through the penetration hole 33 and is accumulated in the cell 31, it causes a variation in resistance or capacitance between the electrode layers 34a and 34b. Thus, the particulate matter may be sensed based on a variation of resistance or electric capacitance between the electrode layers 34a and 34b of the opposing slanted surfaces. The variation of resistance may be measured as an exemplary embodiment, and the variation of capacitance may be measured as another exemplary embodiment.

Figure 3:
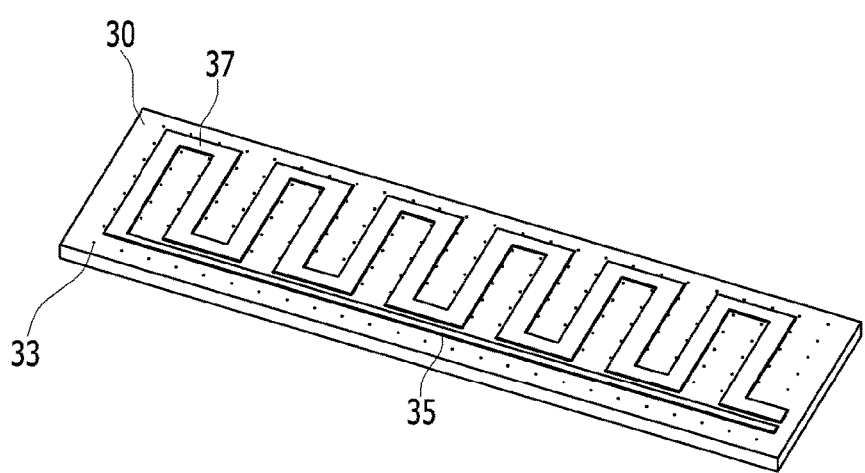
FIG. 3 is a view illustrating a hot wire formed at a rear surface of a conductor according to an exemplary embodiment of the present disclosure.

The conductor 30 includes hot wires 35 and 37 formed at a rear surface thereof as shown in FIG. 3. If a voltage is applied to the hot wires 35 and 37, Joule heat is generated so that power is generated, thereby removing the particulate matter accumulated on the cell. Further, the hot wires 35 and 37 generate a heat stream equal to the power, and the heat stream is radiated to a low temperature part.

FIG. 3 is a view illustrating a hot wire formed at a rear surface of a conductor according to an exemplary embodiment of the present inventive concept.

Referring to FIG. 3, the hot wires 35 and 37 are formed at a rear surface of the conductor 30, and include a first hot wire 35 and a second hot wire 37.

The first hot wire 35 is formed in a longitudinal direction of the conductor 30 and is connected between an end of the conductor 30 and an opposite end of the conductor 30.

The second hot wire 37 is integrally connected to the first hot wire 35, and is formed in a longitudinal direction of the first hot wire 35 in a meandering form.

Accordingly, an influence on the penetration hole 33 formed in the conductor 30 may be minimized by applying the meandering form to the hot wires 35 and 37.

An end of the hot wire 35 and an end of the second wire 37 are exposed to outside so that the hot wire 35 and the second wire 37 may be connected to a power supply.

Accordingly, a particulate material sensor 1 is installed perpendicular to a flow direction of the exhaust gas. When the exhaust gas flows, the particulate matter included in the exhaust gas is accumulated inside the cell 31. The exhaust gas from which the particulate matter is removed is exhausted through the penetration hole 33 and the substrate hole 23.

In this case, the accumulated particulate matter is removed through heat of the hot wires 35 and 37 which are formed at a rear surface of the conductor 30.

The particulate matter sensor detects the accumulated particulate matter as described above to output a signal to a controller (not shown).

Accordingly, the controller may determine whether a diesel particulate filter is broken by determining an amount of the particulate matter.

Since the particulate matter sensor 1 according to an exemplary embodiment of the present inventive concept may concentrate and accumulate the particulate matter included in the exhaust gas on an electrode which is formed on the slanted surface of the cell 31, and may simultaneously remove the particulate matter by applying a bottleneck structure, an initial accumulation time may be reduced.

Accordingly, 90% or more of the particulate matter included in the exhaust gas may be captured.

Further, the particulate matter sensor 1 according to an exemplary embodiment of the present inventive concept includes the diesel particulate matter filter (DPF) of the diesel engine, to be applied to various internal combustion engines such as a gasoline engine, a gas engine, and a bio engine using a biofuel for exhausting the particulate matter.

While this invention has been described in connection with what is presently considered to be practical exemplary embodiments, it is to be understood that the invention is not limited to the disclosed embodiments, but on the contrary, is intended to cover various modifications and equivalent arrangements included within the spirit and scope of the appended claims.

What is claimed is:

1. A particulate matter sensor for an exhaust system of a vehicle comprising:
    a cartridge having an opening;
    a substrate disposed inside the cartridge; and
    a conductor, which is in contact with one surface of the substrate, having a plurality of penetration holes in a flow direction of exhaust gas and including a plurality of cells having an electrode layer,
    wherein a particulate matter included in the exhaust gas is identified based on a variation of resistance or capacitance.

2. The particulate matter sensor of claim 1, wherein each of the plurality of cells has at least one slanted surface which has a width gradually decreasing in a direction toward a rear surface from a front surface of the plurality of cells.

3. The particulate matter sensor of claim 2, wherein:
    the at least one slanted surface includes a plurality of slanted surfaces formed opposite to each other;
    the electrode layer is mounted on each of the plurality of slanted surfaces; and
    the particulate matter is detected based on a variation of resistance or capacitance between the electrode layer of opposing slanted surfaces.

4. The particulate matter sensor of claim 1, wherein each cell is formed at a front surface of the conductor by wet etching.

5. The particulate matter sensor of claim 4, wherein each cell has at least one slanted surface formed by wet etching the conductor, and
    the at least one slanted surface has a slanted angle formed in accordance with a crystalline direction of the conductor.

6. The particulate matter of claim 5, wherein the conductor is made of a silicon wafer, and
    the slanted angle is 54.7°.

7. The particulate matter sensor of claim 1, wherein the substrate has a plurality of substrate holes connected to the plurality of penetration holes, respectively.

8. The particulate matter sensor of claim 7, wherein the penetration hole and the substrate hole have a diameter of 12 μm to 20 μm.

9. The particulate matter sensor of claim 1, wherein a front surface of the conductor is exposed through the opening of the cartridge.

10. The particulate matter sensor of claim 1, wherein the conductor has a hot wire at a rear surface thereof.

11. The particulate matter sensor of claim 10, wherein the hot wire comprises:
    a first hot wire disposed in a longitudinal direction of the conductor; and
    a second hot wire connected to the first hot wire in a meandering form.

12. The particulate matter sensor of claim 1, wherein the substrate is in contact with the conductor through an adhesive layer.

13. The particulate matter sensor of claim 1, wherein the substrate is made of a ceramic material.

* * * * *